(12) United States Patent
Napoli

(10) Patent No.: US 7,594,447 B2
(45) Date of Patent: Sep. 29, 2009

(54) DEVICE FOR TESTING FOR TRACES OF EXPLOSIVES AND/OR DRUGS

(75) Inventor: Joseph D. Napoli, Windham, NH (US)

(73) Assignee: GE Homeland Protection, Inc., Newark, CA (US)

( * ) Notice: Subject to any disclaimer, the term of this patent is extended or adjusted under 35 U.S.C. 154(b) by 322 days.

(21) Appl. No.: 11/402,190

(22) Filed: Apr. 11, 2006

(65) Prior Publication Data

US 2007/0169570 A1    Jul. 26, 2007

Related U.S. Application Data

(62) Division of application No. 10/929,915, filed on Aug. 30, 2004, now Pat. No. 7,047,829.

(51) Int. Cl.
*G01N 1/00* (2006.01)

(52) U.S. Cl. .................. 73/864.81; 73/864.71

(58) Field of Classification Search .............. 73/864.81, 73/864.71
See application file for complete search history.

(56) References Cited

U.S. PATENT DOCUMENTS

| | | | |
|---|---|---|---|
| 3,842,679 A * | 10/1974 | Iwao et al. ............... 73/864.21 |
| 4,045,997 A | 9/1977 | Showalter et al. |
| 4,202,200 A | 5/1980 | Ellson |
| 4,772,794 A | 9/1988 | Jenkins |
| 4,781,972 A | 11/1988 | Sakane et al. |
| 4,896,547 A | 1/1990 | Arney et al. |
| 4,964,309 A | 10/1990 | Jenkins |
| 4,987,767 A | 1/1991 | Corrigan et al. |
| 5,027,643 A | 7/1991 | Jenkins |
| 5,074,157 A * | 12/1991 | Marsoner et al. ......... 73/864.81 |
| 5,109,691 A | 5/1992 | Corrigan et al. |
| 5,200,614 A | 4/1993 | Jenkins |
| 5,405,781 A | 4/1995 | Davies et al. |
| 5,491,337 A | 2/1996 | Jenkins et al. |
| 5,585,575 A * | 12/1996 | Corrigan et al. .......... 73/863.71 |
| 5,591,894 A * | 1/1997 | Falk et al. .................. 73/19.07 |
| 5,741,984 A | 4/1998 | Danylewych-May et al. |
| 5,753,832 A | 5/1998 | Bromberg et al. |
| 5,760,314 A | 6/1998 | Bromberg et al. |
| 5,844,148 A * | 12/1998 | Klein et al. ............... 73/863.82 |
| 5,859,362 A | 1/1999 | Neudorfl et al. |
| 5,859,375 A * | 1/1999 | Danylewych-May et al. ........................ 73/864.71 |
| 5,915,268 A | 6/1999 | Linker et al. |
| 6,073,499 A | 6/2000 | Settles |
| 6,334,365 B1 | 1/2002 | Linker et al. |

(Continued)

FOREIGN PATENT DOCUMENTS

EP    0 247 243    12/1987

*Primary Examiner*—Robert R Raevis
(74) *Attorney, Agent, or Firm*—Global Patent Operation

(57) ABSTRACT

An apparatus is provided for detecting whether a person has handled explosives, narcotics or other substances of interest. The apparatus includes a metallic sample collection surface on which a person may place a finger. Upon removal of the finger, the metallic sample collection surface is moved to a desorber. The desorber heats the metallic surface sufficiently to vaporize residue transferred from the person. The vaporized residue then is transmitted to a detector for analysis. The detector also may include a fingerprint reading apparatus for reading the fingerprint of the person and comparing the fingerprint to known fingerprint data.

4 Claims, 6 Drawing Sheets

U.S. PATENT DOCUMENTS

| | | |
|---|---|---|
| 6,375,697 B2 | 4/2002 | Davies |
| 6,407,382 B1 | 6/2002 | Spangler |
| 6,642,513 B1 | 11/2003 | Jenkins et al. |
| 6,690,005 B2 | 2/2004 | Jenkins et al. |
| 6,831,273 B2 | 12/2004 | Jenkins et al. |
| 6,886,421 B2 * | 5/2005 | Mathur et al. ............ 73/864.81 |
| 6,895,804 B2 * | 5/2005 | Lovell et al. ................ 73/31.05 |
| 2004/0092842 A1 * | 5/2004 | Boecker et al. .............. 600/575 |
| 2004/0131503 A1 | 7/2004 | McGann et al. |

* cited by examiner

DEVICE FOR TESTING FOR TRACES OF EXPLOSIVES AND/OR DRUGS

This application is a divisional of U.S. patent application Ser. No. 10/929,915, filed Aug. 30, 2004.

BACKGROUND OF THE INVENTION

1. Field of the Invention

The invention relates to an apparatus for testing for the presence of trace amounts of a contraband material on a person.

2. Description of the Related Art

Terrorism risks continue to increase at transportation facilities, government buildings, banks, restaurants, hotels and other locations where there is a significant flow of pedestrian or vehicular traffic.

Airlines now routinely screen passengers and employees for explosives. Screening typically is carried out in several stages. For example, all passages are required to pass through a metal detector and all baggage is required to pass through an X-ray apparatus. However, a plastic explosive device could be concealed on a person or in a piece of luggage in a manner that might not be detected by a conventional metal detector or an X-ray apparatus. Even a small amount of a plastic explosive can cause sufficient damage to bring down an aircraft.

Most airports now include apparatus for detecting trace amounts of explosives. These devices operate on the principle that small amounts of the explosive materials will be transferred to the body, clothing and luggage of people who had handled the explosive. Some detectors employ small flexible fabric-like traps that can be wiped across a package or piece of luggage. The trap removes residue from the surface of the package or luggage. The trap then is placed in an apparatus, such as an ion trap mobility spectrometer, that tests the residue on the trap for trace amounts of explosive materials. A device of this type is disclosed in U.S. Pat. No. 5,491,337 and is marketed by the GE Ion Track. These devices typically are employed in proximity to the metal detectors, and security personnel will perform screening on some of the passengers based on a random sampling or based on a determination that the passenger has met certain criteria for enhanced screening.

The ion trap mobility spectrometer disclosed in U.S. Pat. No. 5,491,337 also can operate in a mode for detecting trace amounts of narcotics. Narcotics are illegal and insidious. Furthermore, it is known that many terrorists organizations fund their terrorism through the lucrative sale of narcotics.

The above-described ion trap mobility spectrometer and similar devices have been accepted at airports in view of the notorious efforts of terrorist groups to attack commercial airliners. The above-described detectors have not been accepted widely at other potential targets of terrorism, including train stations, bus terminals, government buildings and the like. The screening of personnel entering train stations, bus depots, government buildings and such by the above-described detection devices would significantly slow the flow of people into and through such buildings and would impose a significant cost penalty on the operators of such facilities.

Only a fraction of airline passengers have their baggage checked for trace amounts of explosives or narcotics using the available ion trap mobility spectrometers and similar devices. Efforts to use such devices to check all bags for trace amounts of explosives or narcotics would impose greater time and cost penalties on the airline industry. Additionally, explosive detectors typically are used only on luggage and other parcels. An apparatus of this type would not identify plastic explosives worn by a passenger who had no carry-on luggage.

U.S. Pat. No. 6,073,499 discloses a walk-through detector. The detector shown in U.S. Pat. No. 6,073,499 operates under the principle that a boundary layer of air adjacent to a person is heated by the person. This heated air adjacent a person is less dense than air further from the person. Less dense air rises. Accordingly, a thermal plume of air flows up adjacent to a person. Minute particles, including particles of explosives or narcotics, will be entrained in this thermal plume of air and will flow upwardly from a person. The walk-through detector disclosed in U.S. Pat. No. 6,073,499 employs an ion mobility spectrometer or ion trap mobility spectrometer to detect microscopic particles of interest that are likely to be entrained in the thermal plume of air flowing upwardly adjacent to a person who walks through and pauses briefly in the detector. The walk-through detector disclosed in U.S. Pat. No. 6,073,499 is very effective for detecting whether a person is carrying explosives or narcotics and whether the person has recently handled explosives or narcotics.

A person who had handled explosives or narcotics is likely to have microscopic residue of the explosive or narcotic materials on his or her fingers, and trace amounts of the explosive or narcotic will be transferred to objects that are handled by the person. U.S. Pat. No. 5,741,984 discloses an apparatus for dispensing tokens that preferably are made of PTFE or cotton. The dispensing apparatus is constructed so that the individual is required to grip the token tightly to separate the token from the dispensing apparatus. The token then is fed into a token handler that delivers the token into an ion mobility spectrometer for analyzing residue that may have been transferred to the token from the hand of the person who retrieved the token from the dispenser. The apparatus shown in U.S. Pat. No. 5,741,984 creates inventory control problems associated with the need for having a sufficient supply of tokens and then periodically loading tokens into the dispenser. Additionally, the system disclosed in U.S. Pat. No. 5,741,984 requires a separate complex dispensing apparatus for dispensing tokens with sufficient resistance for reliably transferring residue from the hand of the person retrieving the token. Additionally, a complex apparatus is required for handling the token, feeding the token into the ion mobility spectrometer and then removing the token after analysis. The inventor of the subject application has determined that residue of such contraband will be transferred from the fingers of the person to an airline ticket, a boarding pass or an identification card. Pending U.S. patent application Ser. No. 10/774,003 discloses a detector that identifies particles of interest on such a card-like object. Accordingly, the device disclosed in pending U.S. patent application Ser. No. 10/774,003 avoids problems associated with maintaining an inventory of tokens, dispensing tokens properly from a dispenser, handling tokens in a token handler and then removing the tokens from the token handler.

The above-described products that check for the presence of trace amounts of substance of interest on luggage, tickets, boarding passes and the like generally work very well. However, there continues to be a demand for a small, rapid, reliable and low cost detector for detecting trace amounts of substances of interest directly on a person. A device of this type would be useful at security checkpoints where a person is not likely to be carrying luggage (e.g., many commuter train stations or bus terminals) and at locations where a person is not likely to have a boarding pass (e.g., government buildings). The above-described walk-through portal provides an unobtrusive checking of passengers for explosives or narcotics without the need to check luggage or boarding passes. However, these devices are relatively large and relatively costly. Hence, devices of this type may be inappropriate for some security checkpoints.

Existing security checkpoints also are very labor intensive, and devices that could reduce the number of highly trained technicians would be received favorably. In this regard, a typical airport security checkpoint requires at least four and typically five or six trained technicians. A first employee reviews personal identification cards and boarding passes at the entry to the checkpoint. A second person coordinates the loading of carry-on luggage and personal effects onto a conveyor for movement through an X-ray scanning device. A third person continuously watches the monitor of the X-ray scanning device. A fourth person controls the movement of passengers through the walk-through metal detector while a fifth person remains available for conducting more detailed screening with a handheld metal detector. The above-described explosive/narcotics detection device that employs fabric-like wipes typically is positioned near the outlet end of the conveyor through the X-ray scanning device. As noted above, the small fabric-like trap is wiped across the surface of the luggage to pick up trace amounts of substances of interest that may have been transferred from the passenger to the luggage. The wipes then are placed in the detector and analyzed. A sixth technician generally is available to perform this screening and analysis. Alternatively one of the five technicians mentioned above must be redeployed for this screening and analysis. A more direct approach would be to detect the substances of interest directly on the passenger. Most preferably, such detection would be carried out without direct human intervention by the technicians who operate the checkpoint.

It is assumed that terrorists and other criminals frequently travel without carrying explosives, weapons or other contraband. Existing security checks at airports compare the name on a boarding pass to the name on a photo identification card and then compare the passenger to the photograph. However, there is virtually no checking of the physical characteristics of the passenger to physical characteristics of suspected terrorists and criminals. Additionally, there is virtually no checking of physical characteristics of the passenger to documented physical characteristics of the person whose name appears on the boarding pass or photographic identification. There is also no checking of whether a person with the physical characteristics of the passenger has traveled previously under a different name.

Devices are available for taking fingerprints of a person and for comparing the fingerprints to information in a database of fingerprint information. Such an apparatus can compare a scanned fingerprint to fingerprints of certain known suspects. Such an apparatus also can store fingerprint data for future reference or analysis. Other apparatus can identify people by scans of facial features or other characteristics.

Accordingly, an object of the subject invention is to provide a device for detecting the presence of substance of interest on a person at a security checkpoint.

Another object of the invention is to provide a device that can check for the presence of a substance of interest without intrusion on the passenger by security personnel.

A further object of the subject invention is to provide an apparatus that can substantially simultaneously check for the presence of a substance of interest and check the identity of the person at the security checkpoint.

An additional object of the invention is to provide a lightweight relatively, low cost, small apparatus for checking for the presence of substances of interest on a person.

Still a further object of the invention is to provide a sampling apparatus where the sampling medium is reusable and non-removably part of the sampling apparatus.

SUMMARY OF THE INVENTION

The subject invention is directed to a detector that can be used at a security checkpoint to check for the presence of explosives, narcotics or other substances of interest on a person. The detector includes a housing and a detecting apparatus within the housing or communicating with the housing. The detecting apparatus preferably is an ion trap mobility spectrometer, such as the detector disclosed in U.S. Pat. No. 5,491,337, the disclosure of which is incorporated herein by reference. A product of this type is marketed by GE Ion Track under the trademark ITEMIZER 3®. The detector also could be an ion mobility spectrometer, such as the type disclosed in U.S. Pat. No. 5,200,614. Other means for detecting trace amounts of explosives, narcotics or other volatile substances can be employed as the detecting apparatus in the detector of the subject invention.

The detector further includes a sample collection assembly for collecting samples directly from a person at the checkpoint and delivering the collected samples to the detecting apparatus so that the samples can be analyzed for substances of interest. The sample collection assembly can be removed and replaced with another type of sample collection assembly, such as the sampling apparatus disclosed in copending application Ser. No. 10/774,003.

The sample collection assembly includes a sampling sheet with a target section dimensioned and configured to accommodate a thumb, a palm or at least one forefinger of a person being screened by the detector. An instruction panel and/or a speaker may be provided in proximity to the sampling sheet to provide visual and/or audible signals instructing the person to place a palm, a thumb or at least one forefinger on the target section of the sampling sheet and/or to wipe a palm, a thumb or at least one forefinger across the target section.

The sample receiver may include a housing with a window disposed so that the target section of the sampling sheet is exposed at the window. The sample collection assembly further includes apparatus for moving the target section of the sampling sheet from the window to an inlet to the detecting apparatus. For example, the sampling sheet may be a generally cylindrical drum, a disc, a plate or a belt. The apparatus that moves the target section of the sampling sheet from the window to the inlet of the detecting apparatus may be an electric motor. The sampling sheet may be deflectable in response to pressure generated by the palm, thumb or forefinger of the person that is being scanned. Removal of the pressure, therefore, may trigger a pressure sensitive switch that activates the motor for moving the target section of the sampling sheet from the window to the inlet of the detecting apparatus. Slots may be provided in the sampling sheet to facilitate deflection.

The sample collection assembly may include a desorber and a transfer box in proximity to the inlet to the detecting apparatus. The target area of the sampling sheet may be advanced into the desorber. The desorber heats the sampling sheet sufficiently to vaporize material transferred from the hand to the target area of the sampling sheet. A vacuum pump then draws the vaporized material into the inlet of the detecting apparatus. The detecting apparatus functions to identify substances of interest and generates a signal when a substance of interest has been detected.

The sample collection assembly may further include a fingerprint scanning device for scanning and reading the fingerprint as finger is wiped across the target area of the sampling sheet. The fingerprints can be stored for future reference. Alternatively, the fingerprint can be compared to known fingerprint data for comparing the scanned fingerprint to other identification information pertaining to the person at the detector. Alternatively, the scanned fingerprint data can be compared to an existing database with fingerprint data for potential terrorists or other criminals. Information obtained by the fingerprint scan can generate an audible or inaudible alarm and can trigger an increased level of scrutiny at the checkpoint.

DETAILED DESCRIPTION OF THE PREFERRED EMBODIMENTS

Figure 1:
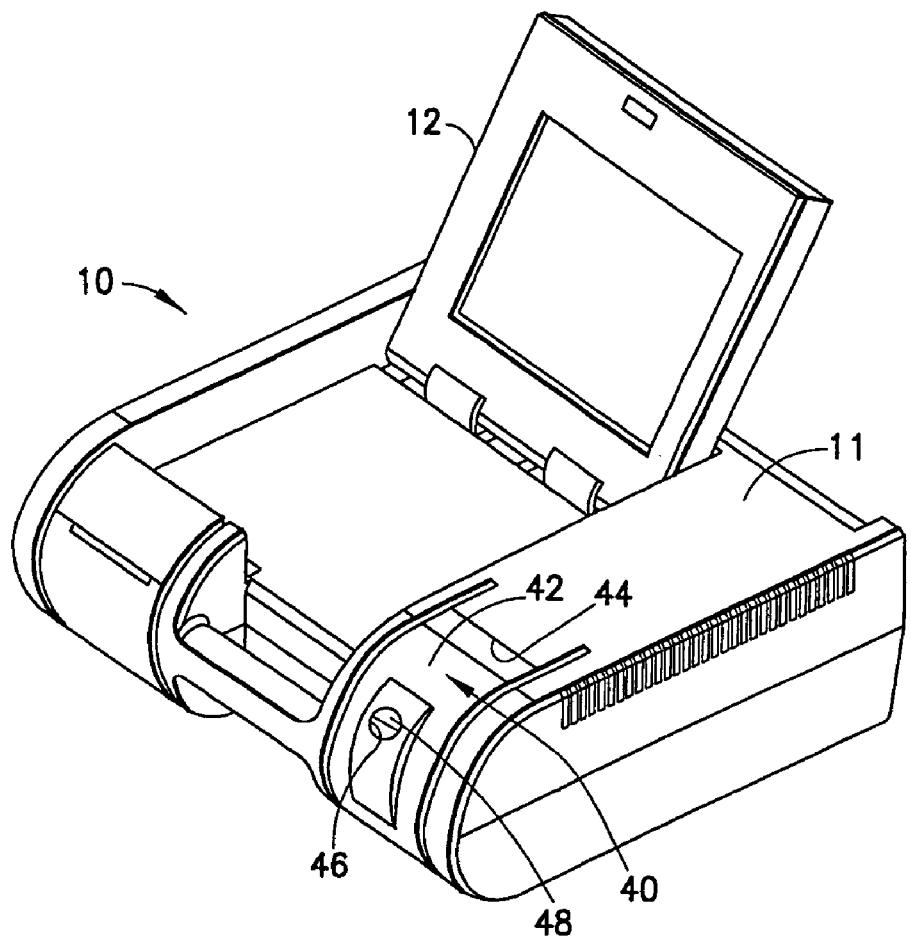
FIG. 1 is a perspective view of a detector that incorporates the apparatus of the subject invention.

A detector according to the invention is identified generally by the numeral 10 in FIG. 1. The detector 10 includes an outer housing 11 and a flat panel display monitor 12 such as an LCD monitor. An ion trap mobility spectrometer (ITMS) is disposed within the housing 11 and is illustrated schematically in FIG. 2.

Figure 2:
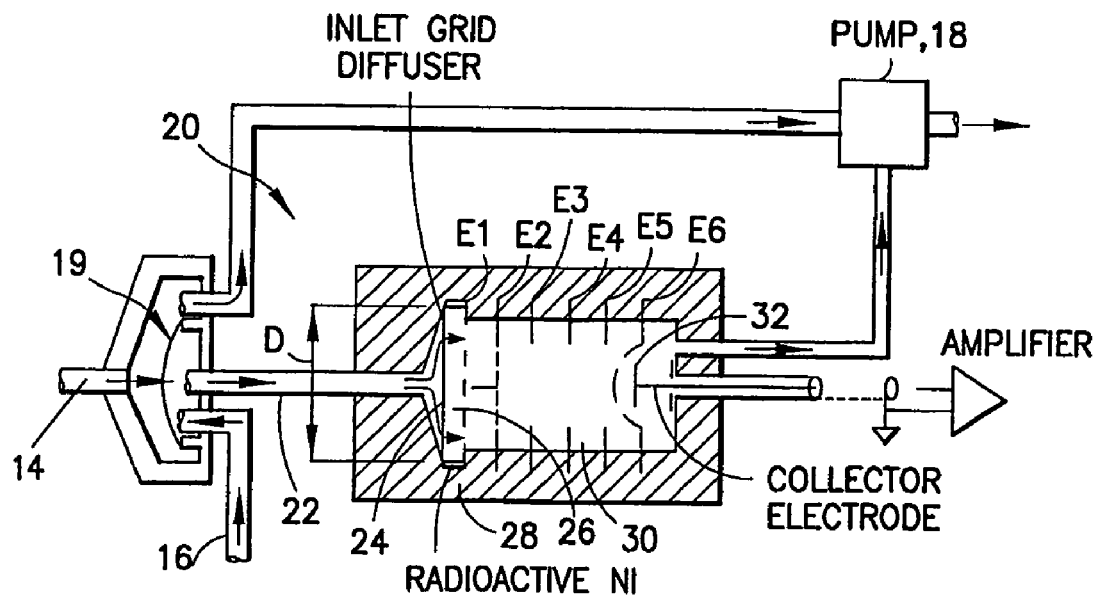
FIG. 2 is a schematic view of an ion trap mobility spectrometer of the detector shown in FIG. 1.
Figure 3:
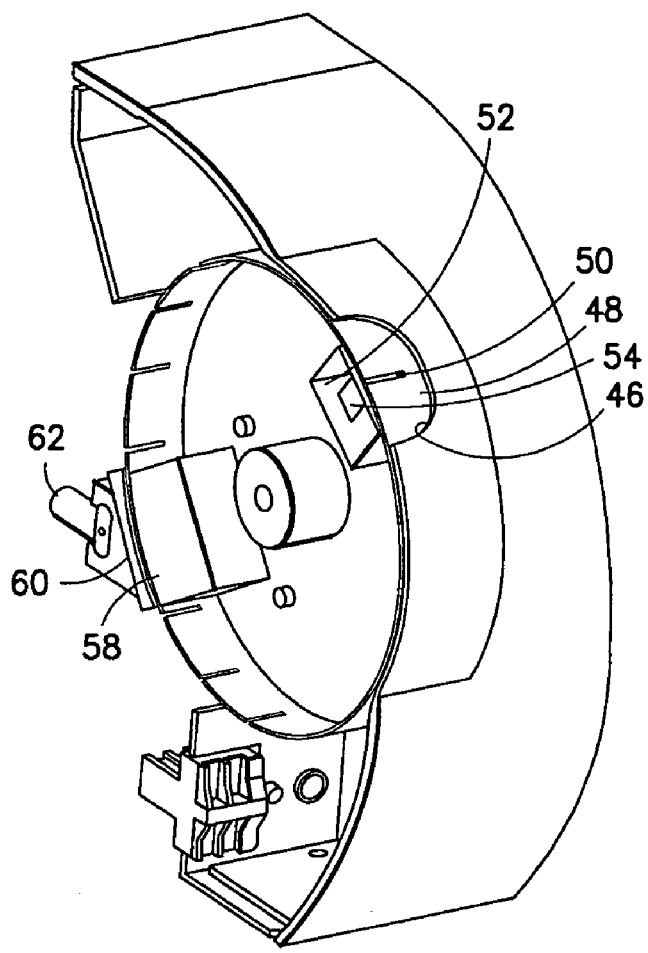
FIG. 3 is a front perspective view, partly in section, of a modular sample collection assembly of the detector for detecting substances of interest on a finger of a person.
Figure 4:
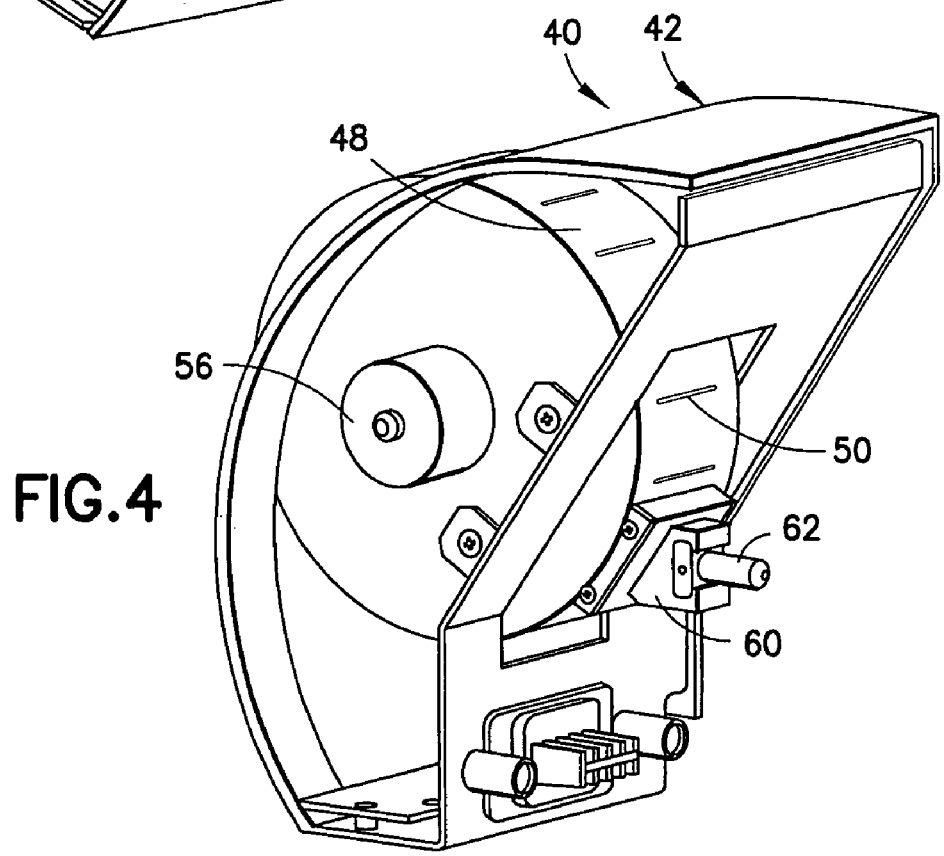
FIG. 4 is a rear perspective view, partly in section of the modular sample collection assembly shown in FIG. 3.
Figure 5:
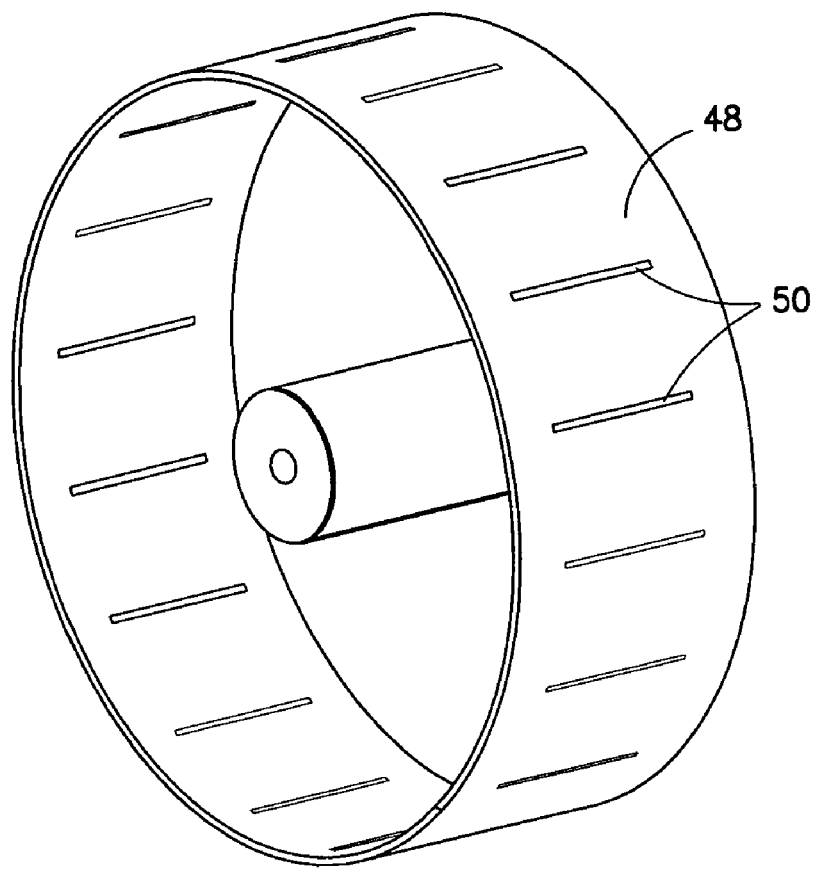
FIG. 5 is a perspective view of a drum for use in the modular sample collection assembly of FIGS. 3 and 4.
Figure 6:
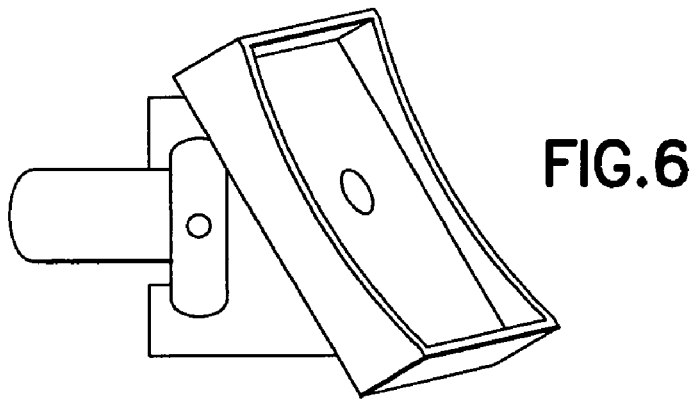
FIG. 6 is a front perspective view of the inlet disposed between the drum of FIG. 5 and the detector of FIG. 2.
Figure 7:
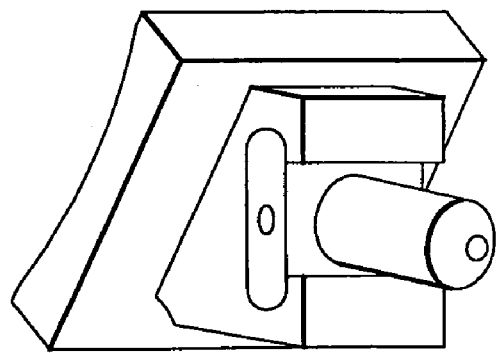
FIG. 7 is a rear perspective view of the inlet shown in FIG. 6.

The ITMS of FIG. 2 comprises a cylindrical detector 20 having an inlet 22 at one end for receiving sample air of interest borne by a carrier gas which that has been doped with a low concentration vapor (typically a few parts per million) employed as a charge transfer mediator. More particularly, the inlet 22 communicates with a source of sample air of interest 14 and a supply of carrier gas and dopant 16 with flows of gases to the inlet 22 being enabled by a flow generator such as a pump illustrated schematically and identified by the numeral 18 in FIG. 2. A heated membrane 19 formed from a microporous refractory material or from dimethyl silicone is disposed near the inlet 22 and in communication with the source of the sample of air 14 for blocking passage of at least selected constituents of the air and for enabling passage of other constituents of the air, including the constituents of interest. The sample air, carrier gas, and dopant molecules pass through the inlet 22 and are spread by a diffuser 24 into an ionization chamber 26. The ionization chamber 26 is in the form of a shallow cylinder with a diameter D, length L, and cylindrical wall 28 of a radioactive material, e.g., nickel$^{63}$ or tritium, which emits beta particles. Inlet 22 communicates with one end of the ionization chamber 26. A grid electrode $E_1$ is provided at the end opposite the inlet 22, and is normally maintained at the same potential as the inlet end and the walls of the ionization chamber 26. Thus a largely field-free space is provided in which electrons and ion charges build up and interact with the sample molecules under bombardment by the beta-particles from the radioactive walls. Beyond the ionization chamber 26, the ionized sample gases pass through open electrode $E_1$ and into an ion drift region 30 having several field-defining electrodes $E_2$-$E_n$. A collector electrode or plate 32 is disposed at the end of the drift region 30 for receiving the ion samples reaching that end.

Periodically a field is established across the ionization region 26, by creating a potential difference between the grid electrode $E_1$ and the inlet diffuser 24 and radioactive source 28, for about 0.1-0.2 mS, to sweep the ions through the open grid $E_1$ into the drift region 30 with the assistance of the switching of the field between electrodes $E_1$ and $E_2$. The ions in the drift region 30 experience a constant electric field, maintained by the annular electrodes $E_2$-$E_n$, impelling them along the region and down toward the collector electrode 32. The electrode 32 detects the arriving charge, and produces signals that are amplified and analyzed through their spectra in the spectrometer. The gases exit through an outlet in the wall next to the electrode 32. After about 0.2 mS the field across the ionization region 26 is again reduced to zero and the ion population is again allowed to build up in the chamber 26 preparatory to the imposition of the next field. The polarity of the fields is chosen on the basis of whether the detector is operated in a negative or positive ion mode. When detecting explosives, a negative ion mode is usually appropriate, but when detecting narcotic samples positive ion mode is preferred.

The detector 10 includes a sample collection apparatus that is identified generally by the numeral 40 in FIGS. 1 and 3-7. The sample collection apparatus 40 include a housing 42 that can be mounted removably into a receptacle 44 formed in the housing 11 of the detector 10. More particularly, the sample collection apparatus 40 is a modular unit that can be releasably mounted to the housing 11 of the detector 10 so that the detector 10 can be adapted for a particular use. In this regard, the sample collection apparatus 40 can be removed and replaced with another sample collection apparatus, such as the card sampling apparatus as identified generally by the numeral 70 in FIG. 10, and as disclosed in copending application Ser. No. 10/774,003. Alternatively, the sample collection apparatus 10 can be replaced with the known apparatus for receiving a fabric-like trap that may be wiped across a surface of a parcel or piece of luggage to detect substances of interest.

The housing 42 of the sample collection apparatus 40 includes a window 46 at a position on the housing 40 that will face the person that is to be scanned for trace amounts of substances of interest. The window 46 is configured and dimensioned to receive substantially all of the gripping surface of the distal digit on a thumb.

The sample collection apparatus 40 further includes a generally cylindrical drum 48 mounted in the housing 42 for rotation about an axis that is parallel to the front face of the detector 10. More particularly, the cylindrical drum 48 is disposed to be substantially internally tangent with portions of the housing 42 adjacent the window 46. Hence, a target area on the exterior of the drum 48 will be exposed at the window 46. The drum 48 is formed from a material that will retain residue from the hand of a person being screened. The material of the drum 48 also must be able to be heated quickly and repeatedly to sufficiently high temperatures for vaporizing residue received from the hand. Additionally, the material of the drum 48 should be capable of being cooled quickly to prevent discomfort when a finger is placed on the drum 48 and to maintain a desirably low cycle time for scanning. The material of the drum can be a non-metallic material or a thin metallic material, such as aluminum or stainless steel. Aluminum exhibits desirable heating and cooling characteristics and exhibits a long life. The thickness of the material of the drum 48 also is selected to facilitate rapid heating and cooling. A thickness in the range of 0.002-0.020 inch is preferred. The relatively thin material of the drum 48 also permits slight inward deflection of the drum 48 in response to digital pressure created by a thumb or forefinger placed on or wiped across the target area of the drum 48 exposed at the window 46. This deflection can trigger a pressure sensitive switch to activate a scanning cycle.

The drum 48 further includes a plurality of slots 50 that extend entirely through the material of the drum 48. The slots 50 perform several functions. The slots 50 remove mass from the drum 48 and break the conductive heat transfer path to facilitate rapid heating and cooling of the drum 48. The slots 50 also accommodate air flow to facilitate cooling. Additionally, the slots 50 facilitate deflection of the drum 48 that may trigger the pressure sensitive switch. Slots 50 that are aligned parallel to the axis of the drum 48 permit the apparatus 40 to accommodate the optional fingerprint scanning. However, embodiments without the fingerprint scanning option can have slots oriented differently or can have perforations other than slots.

The sample collection apparatus 40 further includes a pressure sensitive switch 52 fixedly mounted to the housing 42 at a location radially aligned with the window 46 and inwardly from the drum 48. The switch 52 senses small deflections of the drum 48 as the thumb or forefinger is wiped across portions of the drum 48 in the window 46. Thus, the switch 52 can generate a signal to activate a scanning cycle.

A fingerprint reader 54 optionally is disposed inwardly of the drum 48 for reading fingerprint characteristics of a thumb as the thumb is moved relative to the slot 50. Alternatively, the switch can include an optical switch that will sense the presence of light that occurs when the thumb is slid past the slot 50 and into a position where ambient light can again enter the slot 50.

The sample collection apparatus 40 further includes a motor 56 mounted to the housing and operative to rotate the drum 48. The motor 56 is connected to the switch 52 and functions to rotate the drum 48 a selected amount in response to the sensed completion of a wipe of a thumb or forefinger across portions of the drum 48 disposed in the window 46.

The sample collection apparatus 40 further includes a desorber 58 mounted to the housing and disposed interiorly of and adjacent to the drum 48. The desorber 58 functions to rapidly heat portions of the drum 48 aligned with the desorber 58 for vaporizing trace amounts of material transferred from the thumb or forefinger to the target area of the drum 48 that was exposed at the window 46. The desorber 58 preferably is always on when the detector 10 is on to avoid a need for preheating during each scanning cycle. A sample transfer box 60 is mounted to the housing 42 at a location radially aligned with the desorber 58 but disposed exteriorly of and substantially adjacent the drum 48. The desorber 58, and the sample transfer box 60 have opposed facing surfaces that are curved with radii of curvature substantially corresponding to the inner and outer circumferential shapes of the drum 48. The sample transfer box 60 further includes a sample tube 62 that communicates with the inlet 22 of the ion trap mobility spectrometer of FIG. 2.

The apparatus 10 is employed by providing audible or optically readable instructions to a person who desires access to a restricted or secured area. The optically readable instructions may be provided on the display monitor 12. In particular, the person will be instructed to wipe a thumb across the target area of the drum 48 exposed at the window 46. The fingerprint reader 54, if provided, will optically scan the fingerprint as the thumb is wiped across the slot 50 in the drum 48. The fingerprint data can be stored for future reference. Alternatively, the fingerprint data can be used to compare personal identification information associated with the fingerprint to other personal identification information presented by the user. For example, the identity of the person determined by the fingerprint scan can be compared with identity on an identification card or boarding pass that also is presented to the apparatus 10. An incorrect match may generate a signal to instruct a human security technician to conduct enhanced checking to determine the cause of an inconsistency. Alternatively, the scanned fingerprint data can be compared to known databases that have fingerprints for suspects of terrorism or other crimes. A match with these known databases can generate an audible or inaudible alarm that will trigger additional screening by security personnel or by other available equipment at a security checkpoint.

The movement of a thumb across the target area of the drum 48 exposed at the window 46 will deflect the thin aluminum of the drum 48 and will actuate the pressure sensitive switch 52 aligned with the window 46. Alternatively, a switch can detect changes in light level as the thumb moves clear of the slot 50. The signal generated to indicate a completion of a wipe of a thumb across the target area of the drum 48 in the window 46 will cause the motor 56 to rotate the drum 48 an amount other than 180°, and preferably about 135°. Thus, the target area of the drum 48 that had been aligned with the window 46 will advance into the narrow space between the desorber 58 and the sample transfer box 60. The motor 56 then stops. The heated desorber 58 raises the temperature of the drum 48 between the desorber 58 and the sample transfer box 60 sufficiently to vaporize residue transferred from the thumb to the drum 48. A vacuum pump 18 in the detector of FIG. 2 then will draw the vaporized material through the sample collection tube 62 and into the detector for analysis. The ITMS will detect the presence of substances of interest and will generate an appropriate signal for additional or enhanced testing by security personnel at the checkpoint. The ITMS also can check for "people peaks" indicative of a human being. The absence of a "people peak" may suggest that a person is wearing gloves or has placed a pen or other inanimate object on the drum 48 to avoid an accurate scan. The absence of a people peak may generate a signal for additional screening. The preferred 135° rotation of the drum ensures that the area of the drum 48 that was most recently heated by the desorber 58 will not be rotated directly back into alignment with the window 46. Thus, target areas on the drum 48 are more certain to be sufficiently cool when aligned with the window 46.

Figure 8:
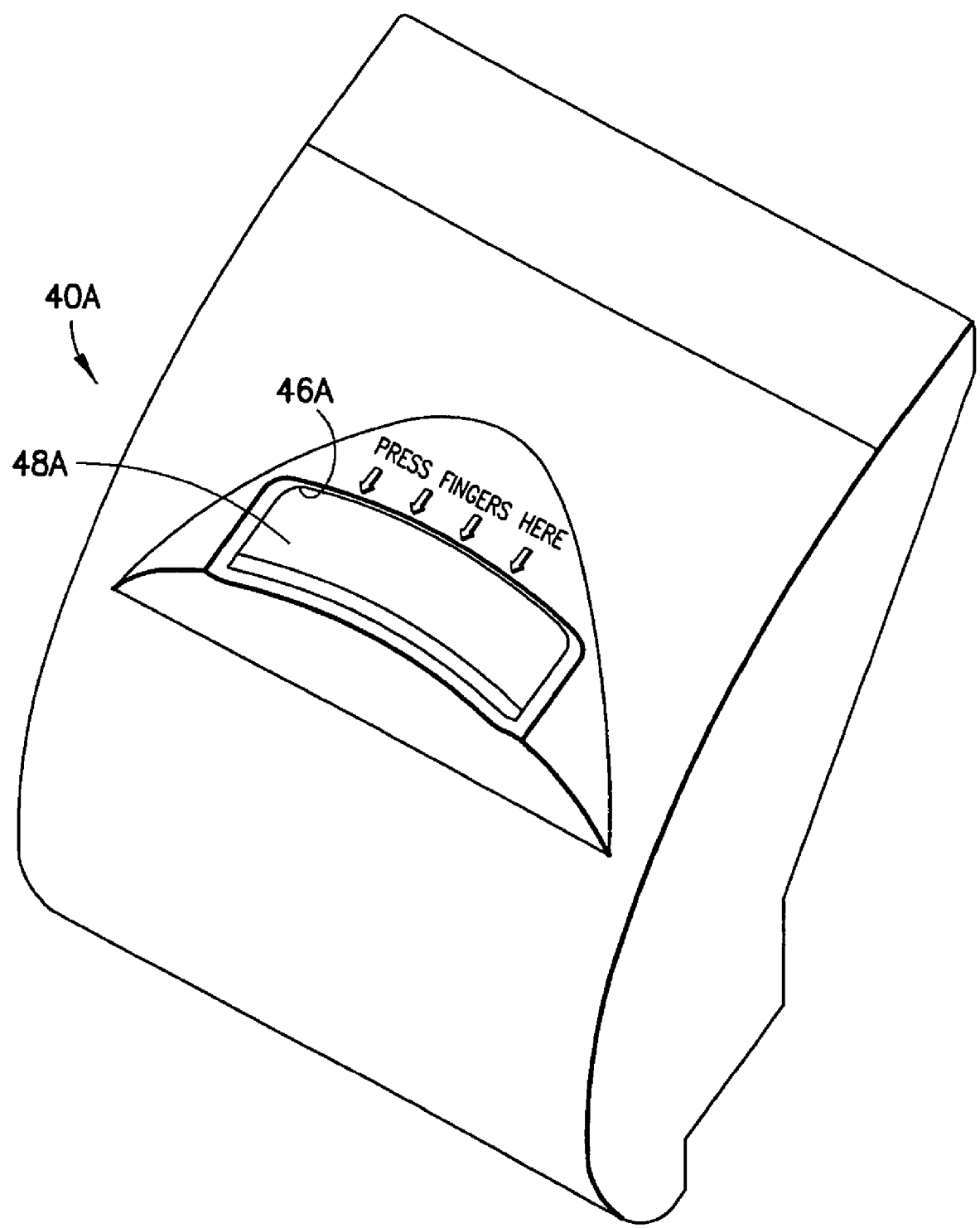
FIG. 8 is a perspective view of an alternate sample collection assembly.
Figure 9:
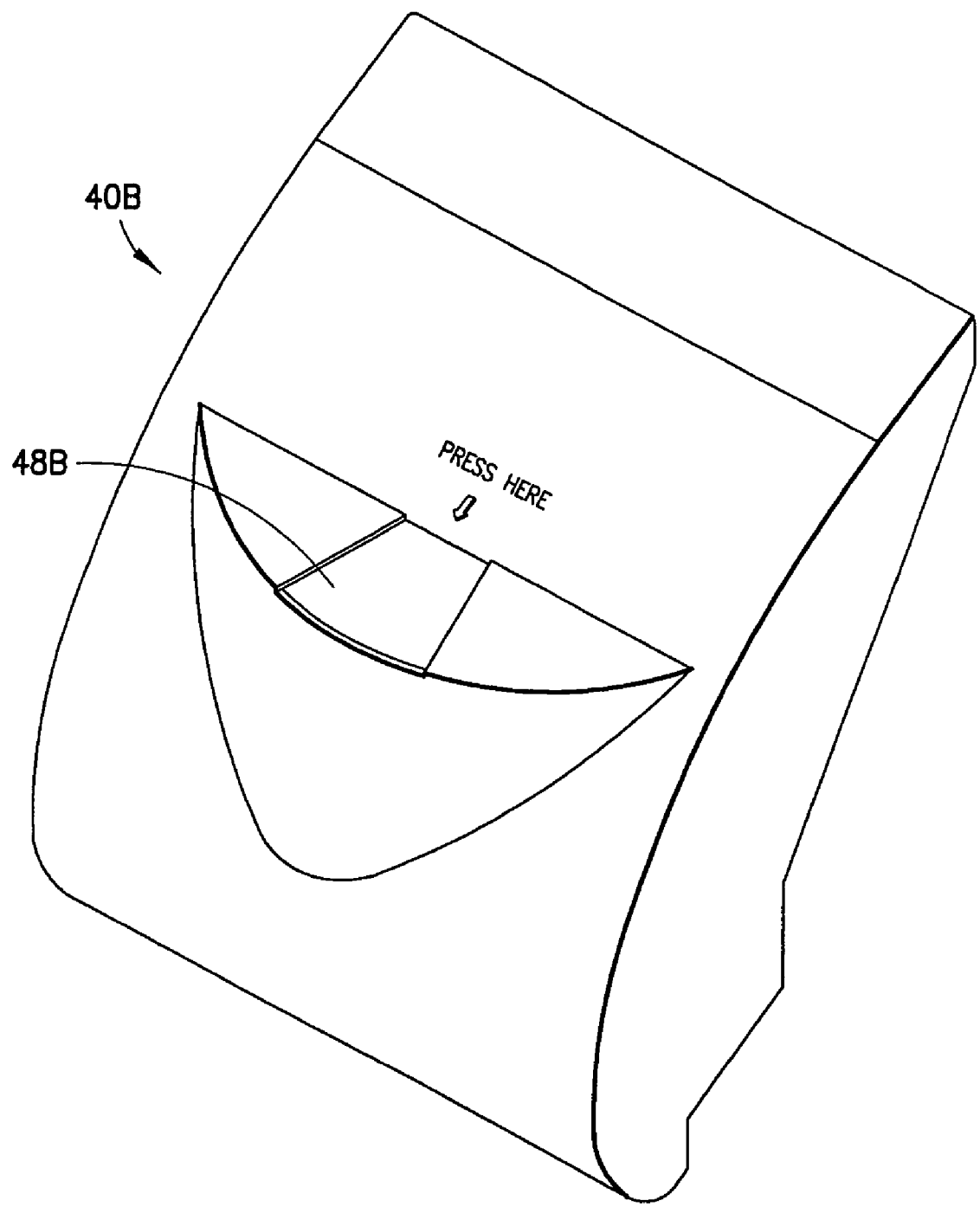
FIG. 9 is a perspective view of another alternate sample collection.

The sample collection apparatus can take other configurations. For example, FIG. 8 shows a sample collection apparatus 40A with a drum 48A mounted for rotation about an axis aligned at an angle, and preferably a right angle, to the front face of the detector 10. The window 46A is sufficiently wide to place all forefingers of one hand on a portion of the drum 48A exposed at the window. FIG. 9 shows a detector 40B with an aluminum disc 48B in place of the drum. The disc 48B rotates about a substantially vertical axis. Other options can include a thin plate that translates without rotation or a flexible belt that is driven about rollers.

While the invention has been described with respect to a preferred embodiment, variations can be made without departing from the scope of the invention as defined by the appended claims.

Figure 10:
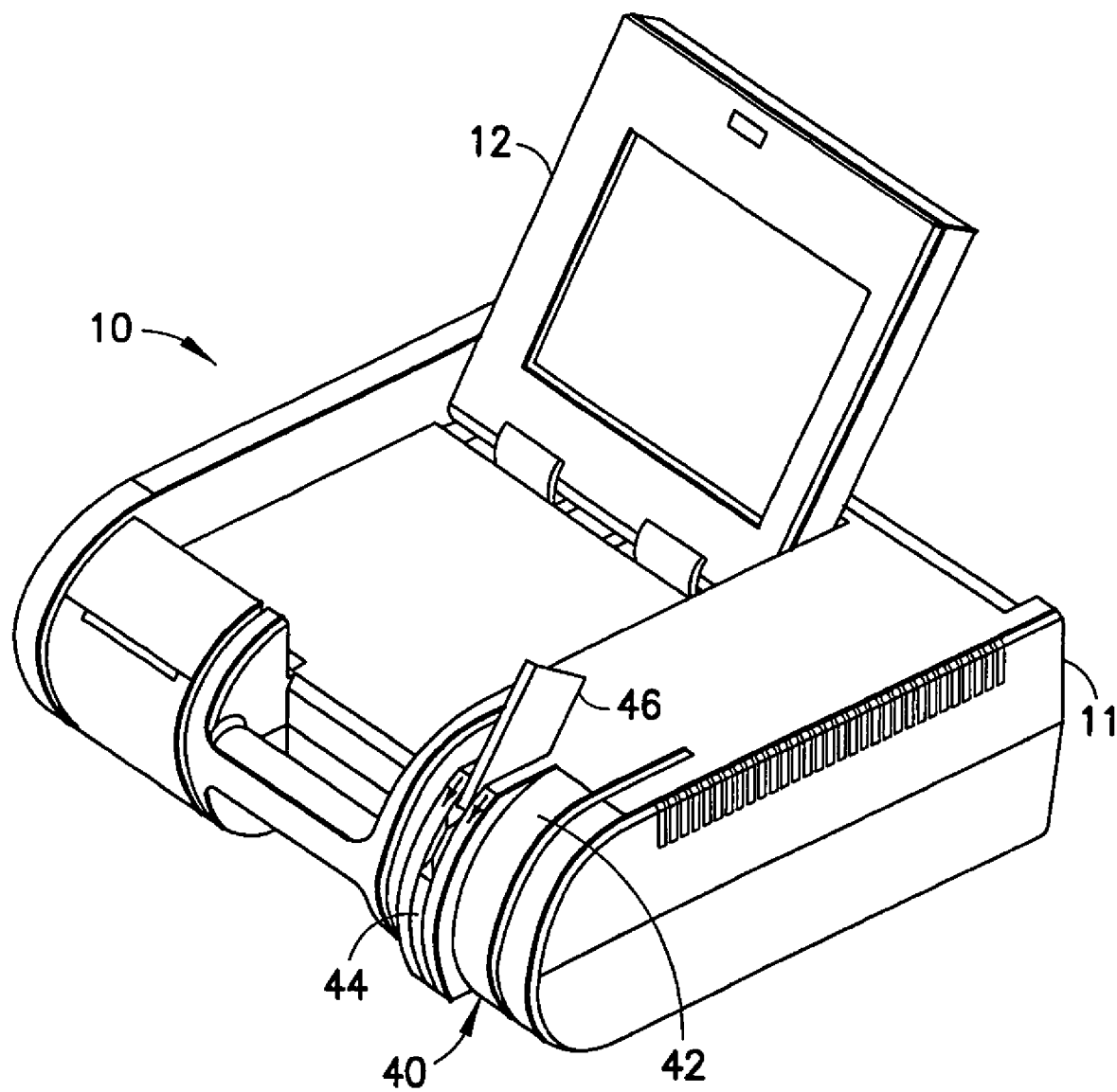
FIG. 10 is a perspective view of the detector with an alternate sample collection assembly mounted therein.

The illustrated apparatus shows the sample collection apparatus 40 as being a modular unit in the detector 10. The sample collection apparatus can be removed and replaced by a card scanner 70, as shown in FIG. 10 and as disclosed in copending application Ser. No. 10/774,003. Alternatively, an apparatus for receiving fabric-like sample traps can be inserted in the receptacle 44. However, the sample collection apparatus 40 can be part of a dedicated detector apparatus without an ability to convert to other testing formats.

The illustrated embodiment of the detector shows a monitor 12 facing generally in the same direction as the window 46. However, the monitor 12 can face in the opposite direction so that a security screener can observe the monitor from one side of the apparatus while a person desiring security clearance will be on the opposed side of the apparatus. Alternatively, a monitor can be disposed at a remote location or can be replaced by or supplemented with other signal generators for indicating clearance or a need for further checking. One monitor can be used to assess scanning performed by a system of detectors 10.

The sampling sheet can be formed entirely from a metallic material, a non-metallic material or combinations of metallic and non-metallic materials. For example, the sampling sheet can include a metallic support at peripheral locations on the sheet and a non-metallic material at intermediate positions.

What is claimed is:

1. A modular detecting system comprising: a housing, a detector in the housing for analyzing a sample to determine whether the sample contains any substances of interest, a first sample collection apparatus configured for receiving a sample residue from a portion of a hand of a person and selectively placing the sample of residue in communication with the detector for analyzing the sample of residue collected directly from the person and a second sample collection apparatus configured differently than the first sample collection apparatus and having an opening for receiving at least a portion of an object and selectively placing a sample collected from the object in communication with the detector for analyzing the sample from the object.

2. The system of claim 1, wherein the first sample collection apparatus includes a drum for receiving contact from part of a hand and a motor for moving the drum into a position for transferring material from the drum to the detector.

3. The system of claim 1, wherein the second sample collection apparatus includes a slot for receiving the object, which object comprises a card, and for removing residue from the card for analysis by the detector.

4. A modular detecting system comprising a housing, the housing being formed with a receptacle, a detector in the housing for analyzing a sample to determine whether the sample contains any substances of interest, the detector having an inlet disposed in the receptacle for receiving the sample, a first type of sample collection apparatus selectively and removably placeable at least partly in the receptacle and a second type of sample collection apparatus selectively and removably placeable at least partly in the receptacle, the second type of sample collection apparatus being configured differently than the first type of sample collection apparatus, the first and second types of sample collection apparatus each having a sample outlet tube that communicates with the inlet of the detector when the first or second type of sample collection apparatus is in the receptacle, wherein the first type of sample collection apparatus is configured for collecting a sample directly from a hand of a person, and wherein the second type of sample collection apparatus is configured for collecting a sample transported by an object other than a person, whereby the first type of sample collection apparatus can be removed from the detector and replaced by the second type of sample collection apparatus.

* * * * *

UNITED STATES PATENT AND TRADEMARK OFFICE
CERTIFICATE OF CORRECTION

PATENT NO.         : 7,594,447 B2
APPLICATION NO. : 11/402190
DATED              : September 29, 2009
INVENTOR(S)        : Joseph D. Napoli It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 493 days.

Signed and Sealed this

Twenty-eighth Day of September, 2010

David J. Kappos
*Director of the United States Patent and Trademark Office*